United States Patent [19]

Dattagupta

[11] Patent Number: 4,670,380

[45] Date of Patent: Jun. 2, 1987

[54] ASSAYS UTILIZING LABELED NUCLEIC ACID PROBES

[75] Inventor: Nanibhushan Dattagupta, New Haven, Conn.

[73] Assignee: Molecular Diagnostics, Inc., West Haven, Conn.

[21] Appl. No.: 612,984

[22] Filed: May 23, 1984

[51] Int. Cl.[4] .................... C12Q 1/68; C12N 15/00
[52] U.S. Cl. ................................. 435/6; 935/78
[58] Field of Search ............... 536/27; 435/4, 6, 7, 435/29, 34, 810; 935/77, 78; 436/501, 518, 530, 94, 800, 824, 828, 536

[56] References Cited

U.S. PATENT DOCUMENTS

| | | | |
|---|---|---|---|
| 4,358,535 | 11/1982 | Falkow | 435/38 X |
| 4,430,318 | 2/1984 | Langone | 436/501 X |
| 4,469,787 | 9/1984 | Woods | 436/808 X |
| 4,469,796 | 9/1984 | Axén | 436/828 X |
| 4,486,539 | 12/1984 | Ranki | 436/804 X |

FOREIGN PATENT DOCUMENTS

| | | |
|---|---|---|
| 0070687 | 1/1983 | European Pat. Off. . |
| 0097373 | 1/1984 | European Pat. Off. . |
| 82/00223 | 7/1983 | PCT Int'l Appl. . |
| 2019408 | 10/1979 | United Kingdom . |

OTHER PUBLICATIONS

McGilvery, R. W., *Biochemistry, A Functional Approach*, W. B. Saunders Co., Philadelphia, 1979, pp. 4, 27-29, 46, 47.

Deibel, M. R. et al., *Anal. Biochemistry*, vol. 144, 1985, pp. 336-346.

Maniatis, T. et al., *Molecular Cloning, a Laboratory Manual*, Cold Spring Harbor Laboratory, N.Y., 1982, pp. 146-147.

van Eekelen, C. et al., *Nucleic Acids Research*, vol. 10, No. 10, 1982, pp. 3039-3052.

Beebe, T. J. C. et al., *Anal Biochem.*, vol. 101, No. 1, 1980, pp. 7-14.

*Primary Examiner*—Esther M. Kepplinger
*Assistant Examiner*—Jeremy Jay
*Attorney, Agent, or Firm*—Sprung Horn Kramer & Woods

[57] ABSTRACT

In a method for determining a particular polynucleotide sequence in a test medium containing single stranded nucleic acids wherein the sample is subjected to a hybridization reaction with a labeled detection probe having a substantially complementary polynucleotide sequence, and wherein after hybridization the label in said probe is assayed, the improvement wherein the label in said labeled probe comprises a fluorescent nucleotide which is linked by a phosphate ester linkage to said probe. Probes and kits therefor are also provided.

2 Claims, 1 Drawing Figure

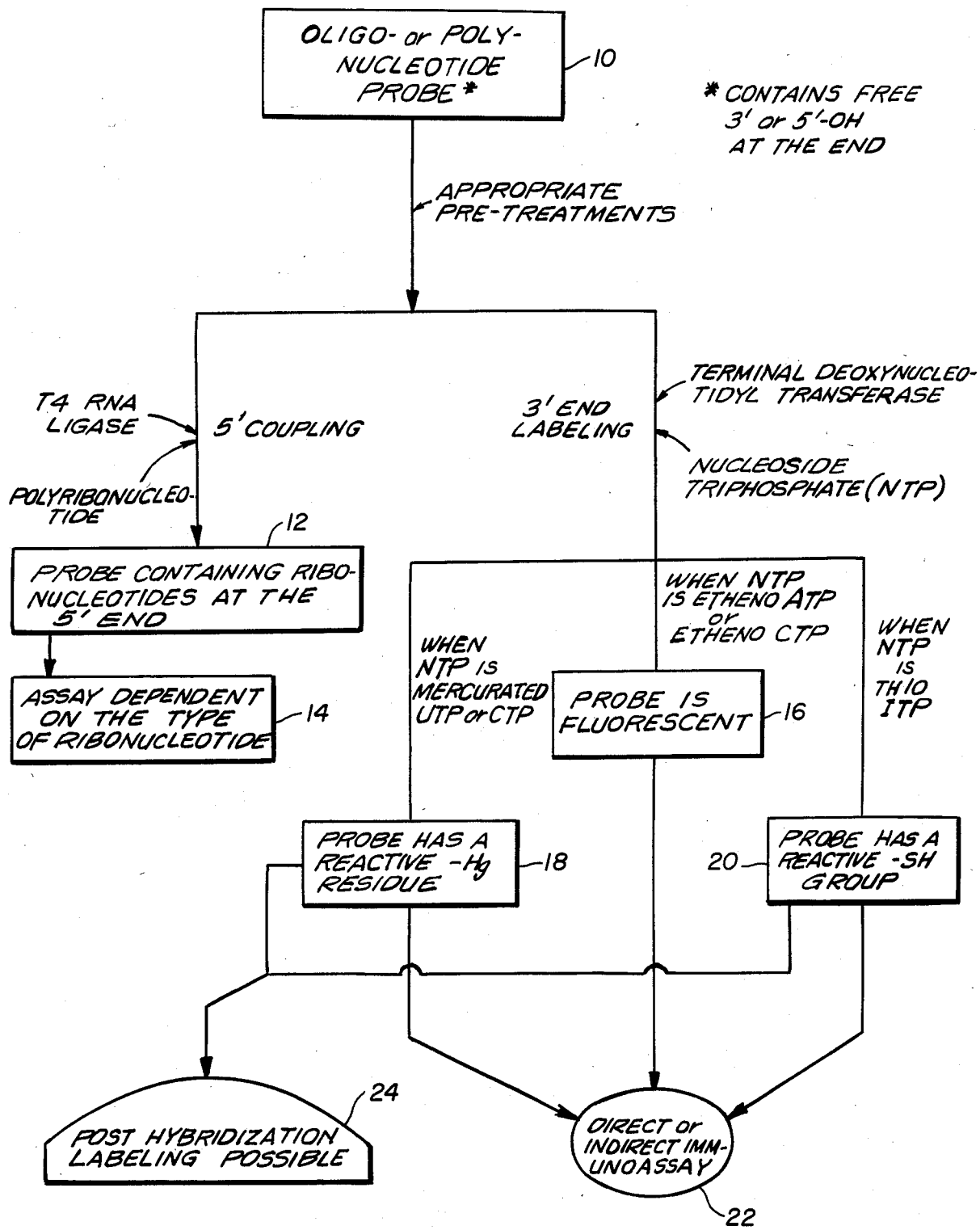

ASSAYS UTILIZING LABELED NUCLEIC ACID PROBES

The invention relates to the labeling of nucleic acid probes and their use in assays.

There are known many techniques for analyzing for the presence or absence of particular genetic conditions, based on the presence or absence of particular nucleic acid sequences in genetic material. These techniques generally involve a hybridization reaction between a test sample and a known reagent known as a probe or detection probe. The probe generally carries a readable label and, after hybridization, either the hybridized material or the residual liquor is analyzed for the amount of label, which is an index of the extent of hybridization, which, in turn, is an index of the amount of the particular nucleic acid sequence in the test sample.

International Patent Application PCT/FR No. 82/00223, International Publication WO No. 83/02277, discloses a method for analyzing for DNA sequences. It comprises the fixing at one of the ends of such DNA a ribonucleotide carrying a molecule covalently fixed and carrying a modification group which may be coupled with an enzyme, allowing a further visualization thereof in presence of a terminal DNA transferase, treating said DNA with different chemical agents allowing to operate differential cleavages within such DNA at the basis, which are also of respectively distinct natures, collecting and separating the DNA fragments carrying the visualizable groups in a system allowing to sort them by the size, and determining the unmodified terminal nucleotides of said DNA fragments, considering the nature of the chemical agents used for the cleavage at their respective levels.

Another test procedure involves contacting the test sample with a solid support carrying a nucleic acid (a separation probe) and with a detection probe carrying a different nucleic acid and a label. If the test sample has the desired nucleotide sequence, it will dually hybridize, i.e., it will hybridize with the two nucleic acid fragments and thereby fix the label to the solid support. Such a technique is described in greater detail in Application Ser. No. 511,063, filed July 5, 1983, now pending.

Great sensitivity is realized if the detection probe carries a radioactive site and the ultimate assay is based on the amount of radioactivity. This presents certain hazards to the operators as well as a waste disposal problem. Further, many laboratories are just not equipped to conduct such assays.

It is accordingly an object of the present invention to provide a nucleic acid-containing detection probe which is useable in an assay with high sensitivity by virtue of the presence of a particular label which is directly readable or which, after hybridization, can be reacted to attach a readable label.

These and other objects and advantages are realized in accordance with the present invention pursuant to which there is provided a detection probe comprising a nucleic acid having a predetermined nucleotide sequence suitable for hybridization and a nucleotide linked by a phosphate ester linkage to the nucleic acid, the nucleotide itself being a readable label or ultimately being reacted upon to add on or form a readable label.

The coupled nucleotide can be a polyribonucleotide, for example, coupled to the 5' end of the oligo or polynucleotide probe by an enzyme such as T4 RNA ligase, and could be directly readable.

Alternatively, the nucleotide can be a nucleoside triphosphate residue coupled to the 3' end as by a terminal deoxynucleotidyl transferase. If the nucleotide is a triphosphate such as etheno ATP or CTP, it will constitute a directly-readable label, being fluorescent. On the other hand, the nucleoside triphosphate may carry a Hg or SH radical, as on the purine or pyrimidine ring, which radical can subsequently be read chemically or preferably is further reacted to provide a readable label. The ultimate label can be an antigen or hapten for immunoassay, a fluorescent moiety, a ligand, a radioactive moiety or an enzymatically operating label such as an enzyme or enzyme co-factor, all in known manner.

The Hg or SH radical can be provided by employing a nucleoside triphosphate such as thio-ITP or mercurated UTP or CTP or the like, and the ultimate linkage can be through —S—Hg or —S—S—.

In accordance with another aspect of the invention the hybridizable nucleotide sequence can be linked to the label through a protein, e.g., protein A, polylysine, polyarginine, bovine serum albumin and avidin. The ultimate label can be an antigen or hapten for immunoassay, a fluorescent moiety, a ligand, a radioactive moiety or an enzymatically operating label such as an enzyme or enzyme co-factor, all in known manner.

In accordance with one aspect of the invention, the ultimate linkage to attach the readable label is not effected until after the hybridization reaction with the test specimen. In that way the label, which could be quite large, will not be present to interfere with the hybridization.

In accordance with yet another aspect of the invention, in a method for determining a particular polynucleotide sequence in a test medium containing single stranded nucleic acids wherein the sample is subjected to a hybridization reaction with a labeled detection probe having a substantially complementary polynucleotide sequence, and wherein after hybridization the label in said probe is assayed, there is provided the improvement wherein the label in said labeled probe comprises a fluorescent nucleotide which is linked by a phosphate ester linkage to said probe.

The label may comprise a nucleotide coupled to the 3' or 5' end of the probe. The fluorescent nucleotide may be derived from nucleoside triphosphates, e.g., etheno ATP, etheno CTP, or the like, and a reactive Hg or SH site may be utilized to effect joinder of the fluorescent moiety to the residue of the nucleoside triphosphate, such residue then being mercurated UTP, mercurated CTP or thio-ITP.

In accordance with another aspect of the invention, a kit is provided to carry out the method, the kit comprising a detection probe as described, plus a support for immobilizing a sample nucleic acid or a support which already carries an immobilized separation probe, the separation probe being complementary to a different portion of the test sample DNA than the detection probe.

The invention will be further described with reference to the accompanying drawing which is a schematic flow sheet showing the production and use of the labeled detection probes in accordance with the present invention.

Referring now more particularly to the drawing, the starting material 10 is an oligo - or polynucleotide probe having a predetermined nucleotide sequence. It may be appropriately pretreated to provide "clean" 3' and/or 5' hydroxyl ends and/or to remove undesired material.

In the left-most branch the starting material is selectively coupled at its 5' end to a polyribonucleotide employing an enzyme such as T4 RNA ligase to produce a probe 12 carrying a ribonucleotide at one end. The labeled probe can be employed in a test in known manner after which the ribonucleotide can be directly read in certain instances at 14, depending upon the particular composition. The polyribonucleotide may contain fluorescent nucleotide residues or a nucleotide residue with an Hg or S residue which can be subsequently fluorescently labeled. The fluorescent nucleotide may be derived from nucleoside triphosphates, e.g., etheno ATP, etheno CTP, or the like, and a reactive Hg or SH site may be utilized to effect joinder of the fluorescent moiety to the residue of the nucleoside triphosphate, such residue then being mercurated UTP, mercurated CTP or thio-ITP.

In the right-most branch, an enzyme such as terminal deoxynucleotidyl transferase is employed to attach a nucleotide, e.g., a nucleoside triphosphate residue, to the 3' end. If the coupled nucleotide is fluorescent, e.g., etheno ATP or CTP, then the material constitutes a directly readable probe 16.

Instead, however, the nucleoside triphosphate can carry a mercury atom, e.g., mercurated UTP or CTP, so that the labeled probe 18 be further reacted, if desired. Alternatively, the nucleoside triphosphate may carry a thiol group, generally on the purine or pyrimidine ring, e.g., thio-ITP, so that the labeled probe 20 also can be further reacted.

The probe 18 or 20 can be reacted with an Hg or S containing readable label, such as a suitable hapten, to form —Hg—S— or —S—S— bonds, the hapten ultimately being readable in immunoassays 22 in conventional manner.

Alternatively, the probe 18 or 20 can be used in hybridization testing in known manner and thereafter reacted through the Hg or SH moiety to add the readable label 24 so that the readable label cannot interfere with the hybridization.

The conditions for carrying out the individual steps are conventional, well-known and capable of wide variation.

The initial polynucleotide probe could be of the type employed in testing for sickle cell anemia genetic bias and the like.

The invention will be further described in the following illustrative examples wherein all parts are by weight unless otherwise expressed.

EXAMPLE 1

Terminal transferase reaction to couple ribonucleoside triphosphates to the 3' hydroxy end of the detection probe The method described below, can be used for DNA, double or single stranded; oligonucleotide and both ribo- and deoxyribonucleotides can be coupled. The reaction has been performed with ribonucleotides comprising adenosine 5' triphosphate, uridine 5' triphosphate, ethenoadenosine and ethenocytidine 5' triphosphates, 5-mercuric uridine 5' triphosphate and 6-mercapto purine riboside 5' triphosphate. A typical reaction is described below. The detection probe of the example of application Ser. No. 511,063, supra, is dialyzed in terminal transferase buffer (200 mM potassium cacodylate, pH 7.2) and the concentration of DNA is adjusted to $10^{-4}$ in base pairs. 100 µl of the DNA solution is mixed with 10 µl of 2 mM dithiothreitol, 1 µl 10 mM nucleoside triphosphate (to be coupled) and finally 10 µl of 10 mM cobalt chloride. The mixture is activated by incubation at 37° C. for 5 minutes, then chilled in ice for 10 minutes. 15 units of terminal deoxynucleotidyl transferase (purchased from P.L. Biochemicals) is added and the mixture is incubated at 15° C. for 60 minutes. After the reaction, the enzyme is removed by phenol extraction in conventional manner. The DNA product is purified on a Sephadex G50 column in potassium cacodylate buffer in conventional manner. The unreacted triphosphates and other materials can be removed from the DNA product by dialysis. Finally the product is precipitated with ethanol and stored solid at −80° C. before use.

EXAMPLE 2

Labeling of mercurated nucleotides with proteins, enzymes or similar compounds can be done by identical procedures. A typical example is given with protein A.

Since the specific interaction of —Hg— and —S— with each other requires that the corresponding partner should contain the respective reactive groups, a mercaptonucleotide can bind a protein carrying a mercuri or mercapto residue. The reverse is true for mercurated nucleotides. The protein A example is unique and universal. This is because protein A lacks —SH residues and it binds several classes of IgG's which can be used to read the label. Before protein A can react with —Hg and —SH, radicals, it is modified with 3-(2-pyridyldithio)propionate (SPDP). 5 mg of protein A (purchased from Pharmacia Fine Chemicals) is dissolved in 5 ml 10 mM potassium phosphate buffer (pH 8). To this solution, 100 µl SPDP (20 mM in ethanol) is added. The mixture is kept at room temperature (25°±2° C.) for six hours. The product is purified on a G-25 column. The product is collected in the excluded volume. The product is then thiolated just before use. Since protein A does not have any disulfide linkage, thiolation can be done at any pH between 4-9, by adding dithiothreitol or other low molecular eight thiol (2-5 mM final concentration) and chromatographic separation of unreacted thiol is done on a gel filtration Sephadex G-25 column.

When the thiolated protein is added to mercurated or mercapto nucleotide or polynucleotide before or after nucleic acid hybridization it will bind to the corresponding specific partner and can be assayed as described in Example 4.

EXAMPLE 3

Coupling of protein A to ribonucleotide via redox reaction

It is known that cis-diols can be oxidized by pertodate to form dialdehydes. The dialdehydes can form Schiff's base with a primary amine group via the addition of —NH$_2$. The Schiff's base can be reduced with sodium boronydride to form a secondary amine.

In a similar manner, nucleic acids (DNA or RNA) containing a ribonucleotide at the 3'-hydroxyl terminus are dissolved in or dialyzed into sodium acetate buffer, 0.1M, pH 5 at a concentration of 1 mM. Twenty (20) µl of sodium metaperiodate (100 mM) is added to 1 ml of nucleic acid solution. The reaction is allowed to proceed for 40 minutes at room temperature (25° C.). Following the reaction, the pH is adjusted to 8 with sodium hydroxide solution. The solution is added to protein A (2 mg in 1 ml buffer) suspended in a suitable buffer such as 0.1M sodium acetate, pH 8. The reaction is allowed to proceed for 30 minutes at room temperature (25° C.) resulting in the formation of a suspension of Schiff's base. The Schiff's base is reduced by the addition of sodium borohydride. The reduction is carried out in four steps: Approximately 0.15 ml of freshly prepared sodium borohydride solution (200 mM) is added and the reaction is allowed to proceed for 30 minutes. Approximately 0.15 ml of the sodium borohydride solution is again added to the reaction mixture and the reaction is continued for 60 minutes. Another 0.15 ml of the sodium borohydride is subsequently added to the reaction mixture. After 90 minutes, another aliquot of 0.15 ml of the sodium borohydride solution is added to complete the reaction. The suspension is centrifuged for 30 minutes at 2000 g. The supernatant is decanted and the wash is repeated 3 times. The pellet is resuspended in 5 ml of the hybridization buffer. Etheno ATP or $^{14}$C ATP residues coupled to single stranded DNA can be used to determine the efficiency of coupling.

EXAMPLE 4

Use of Sickle cell probe and hybridization using the end labeled nucleic acid and detection of protein A The detection probe of application Ser. No. 511,063, supra, is labeled with protein A and hybridized as described in the example of application Ser. No. 511,063, supra. After hybridization, the nitrocellulose paper is soaked in 1 mg/ml bovine serum albumin solution and FITC labeled or radioactively labeled IgG is added, washed with phosphate buffer and photographed under uv lamp using a red filter and polaroid MP4 camera. When radioactive IgG is used, autoradiographic method is used in conventional manner. The quantitative analysis can be done by scanning the negatives.

EXAMPLE 5

Use of end labeled Sickle cell probe for hybridization

The detection probe as in Example 4 is labeled with fluorescent etheno ATP or etheno CTP as in Example 1. Then hybridization is carried out with the labeled probe as in Example 4. After hybridization, the nitrocellulose paper is soaked in a solution containing 0.1 M sodium hydroxide at 60° C. for 30 minutes. The solution is centrifuged, the supernatant is neutralized with HCl and the fluorescence of the ethenonucleotides released is measured in a spectrofluorimeter SLM 4800. Excitation and emission wavelengths are 320 and 400 nm respectively. The nitrocellulose paper can be soaked in large excess of NaOH solution: 0.1 to 5 ml per cm$^2$ surface area. If the volume is large and the intensity of fluorescence is low, the solution after the reaction can be concentrated in a rotary evaporator or in a similar device before or after HCl neutralization. Fluorescence in excess of a threshhold level indicates the patient has Sickle cell anemia.

It will be understood that the specification and examples are illustrative but not limitative of the present invention and that other embodiments within the spirit and scope of the invention will suggest themselves to those skilled in the art.

What is claimed is:

1. In a method for determining a particular polynucleotide sequence in a sample containing single stranded nucleic acids wherein the sample is subjected to a hybridization reaction with a labeled detection probe having a complementary polynucleotide sequence to the nucleotide sequence in the sample, and wherein after hybridization the label of said probe is assayed, the improvement wherein the label of said probe comprises a fluorescent nucleotide which is linked by a phosphate ester linkage at end of said probe, wherein the fluorescent nucleotide is selected from the group consisting of an etheno ATP moiety and an etheno CTP moiety.

2. In a method for determining a particular polynucleotide sequence in a sample containing single stranded nucleic acids wherein the sample is subjected to a hybridization reaction with a labeled detection probe having a complementary polynucleotide sequence to the nucleotide sequence in the sample, and wherein after hybridization the label of said probe is assayed, the improvement wherein the label of said probe comprises a fluorescent nucleotide which is linked by a phosphate ester linkage at end of said probe, wherein the fluorescent moiety is connected to a residue of a nucleoside triphosphate by a reactive Hg or SH site and wherein said nucleoside triophosphate is mercurated UTP, mercurated CTP or Thio-ITP.

* * * * *